(12) United States Patent
Ramos-de-la-Peña et al.

(10) Patent No.: US 8,376,740 B2
(45) Date of Patent: Feb. 19, 2013

(54) ORTHODONTIC BRACKET

(75) Inventors: Alejandro Ramos-de-la-Peña, Monterrey (MX); Pedro-Nicolás Menchaca-Flores, Monterrey (MX)

(73) Assignee: Asociacion Metropolitana Para la Educacion, Nuevo Leon (MX)

( * ) Notice: Subject to any disclaimer, the term of this patent is extended or adjusted under 35 U.S.C. 154(b) by 0 days.

(21) Appl. No.: 13/185,051

(22) Filed: Jul. 18, 2011

(65) Prior Publication Data
US 2013/0022935 A1 Jan. 24, 2013

(51) Int. Cl.
*A61C 3/00* (2006.01)
(52) U.S. Cl. ......................................................... 433/10

(58) Field of Classification Search ................. 433/8–17
See application file for complete search history.

(56) References Cited

U.S. PATENT DOCUMENTS

2007/0224569 A1* 9/2007 Oda .............................. 433/10
2007/0248928 A1* 10/2007 Damon ......................... 433/10

* cited by examiner

*Primary Examiner* — Heidi M Eide
(74) *Attorney, Agent, or Firm* — Young & Thompson (57) ABSTRACT

An Orthodontic bracket wherein an opened channel receiving an orthodontic wire, includes covering element to cover the opened channel, the covering element can be opened to allow a fast and easy insertion of the orthodontic wire into the channel and can be closed and blocked to avoid that the wire goes out from the channel.

4 Claims, 7 Drawing Sheets

ORTHODONTIC BRACKET

BACKGROUND OF THE INVENTION

A. Field of the Invention

This invention is related to orthodontic brackets and, more particularly, to an orthodontic bracket wherein an opened channel, which receives an orthodontic wire, includes means to cover said channel. The cover means can be opened to allow a fast and easy insertion of the orthodontic wire into the channel and can be closed to block the wire from going out of the channel.

B. Description of the Related Art

Orthodontic brackets are well known in the art. Prior art brackets are cemented over the teeth to receive a tensioned wire and act as strength transmitters to move and align the teeth to a suitable aesthetic and functional position.

Normally, most of the existing bracket designs do not allow a simple installation of the orthodontic wires. Additionally, in some of said designs, the wires tend to go out from the bracket causing problems in the orthodontic treatment.

In view of the above mentioned problems, some bracket designs have been suggested which include means to cover the channel wherein the orthodontic wire is housed, which cover means can be opened and closed to easily insert or remove the orthodontic wire from said channel.

Examples of said brackets are disclosed in the following U.S. Pat. Nos. 5,269,681, 5,322,435, 5,516,284, 6,368,105, 6,960,080, 6,960,081, 6,964,565, 7,210,927, 7,210,928, 7,234,935, 7,419,375, 7,674,110, and in the following U.S. patent applications: 20040209219, 20070243497, 20090298003, 20100055636.

However, these brackets, due to the particularities of their designs, there is the possibility that the means to cover the channel of the bracket open and release the wire because they do not include reliable blocking or gripping means, if they include them.

In view of said problem, applicant developed an orthodontic bracket wherein the opened channel which receives the orthodontic wire includes means to cover said channel, which cover means include blocking means to avoid opening of the said cover means to avoid the wire leaving the channel.

The blocking means act directly on the means to cover the channel, resulting practically impossible to open said cover means unless said blocking means be retired, which blocking means are actuated by means of a spring element maintaining them in place, by which the possibility that the means to cover the channel, open and the wire leave the channel, is practically inexistent.

SUMMARY OF THE INVENTION

It is therefore a main object of this invention, to provide an orthodontic bracket wherein the opened channel which receives the orthodontic wire, includes means to cover said channel which in turn includes blocking means to avoid that said cover means open and the wire can go out from the channel.

It is another main object of this invention, to provide an orthodontic bracket of the above disclosed nature wherein the blocking means act directly on the means to cover the channel, resulting impossible to open said means unless said blocking means be retired, which are actuated by means of a spring element maintaining the wire in its place, by which the possibility that the means to cover the channel, open and the wire leave the channel, is practically inexistent.

These and other objects and advantages of the rotary bracket of this invention, will be clear to those persons having ordinary skilled in the art, from the following detailed description of the invention, which will be with reference to the accompanying drawings.

DETAILED DESCRIPTION OF THE INVENTION

Figure 1:
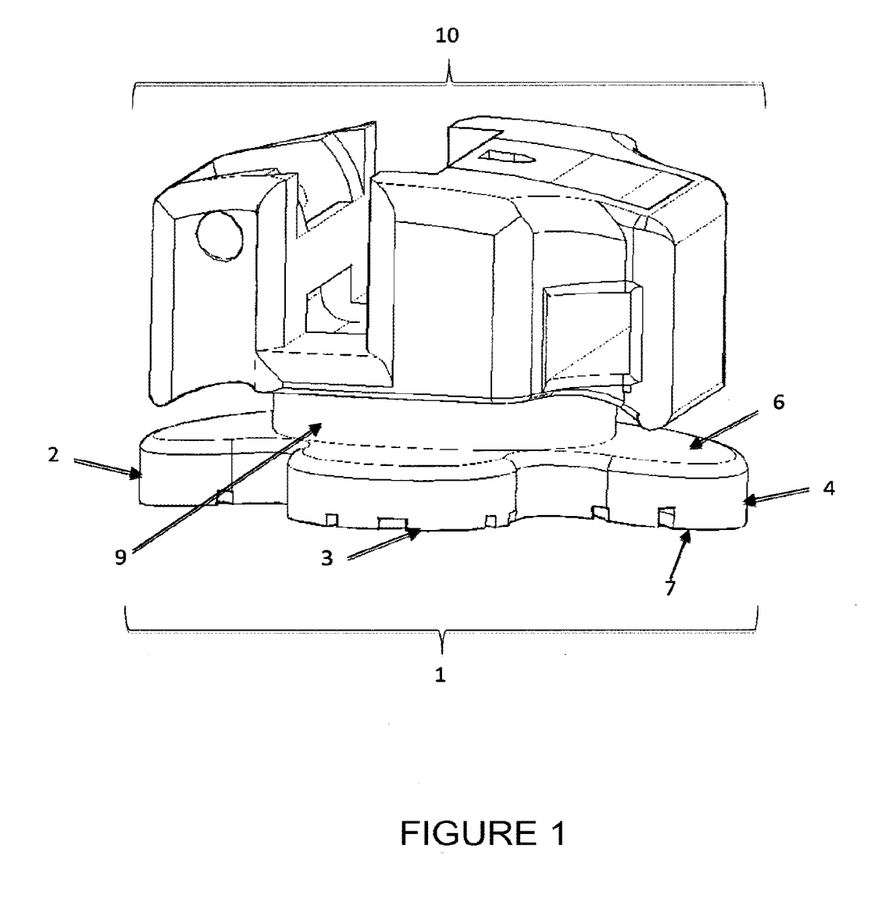
FIG. 1, is a perspective view of the orthodontic bracket of the present invention, without including the means to cover the channel, but including the sliding lid of the gripping means.
Figure 2:
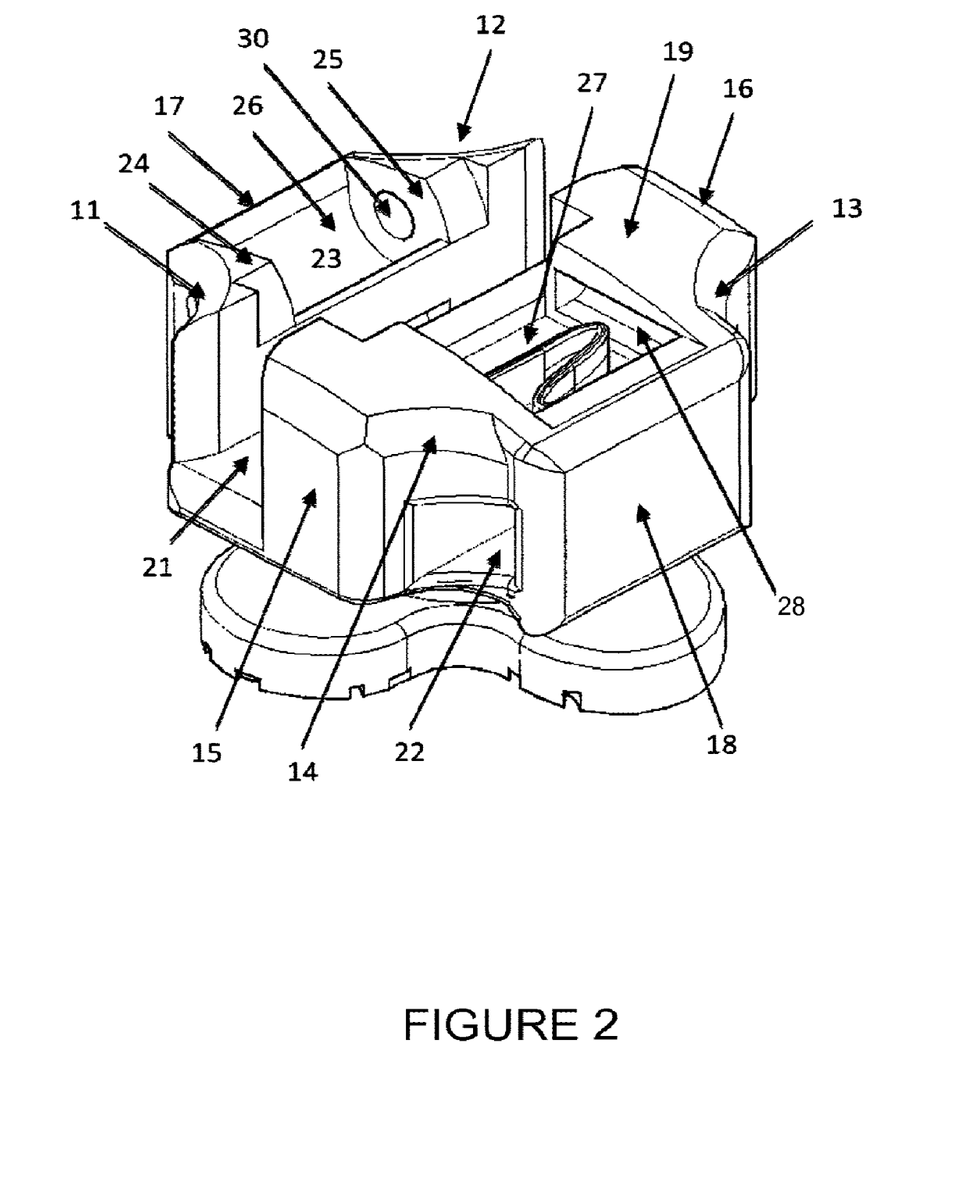
FIG. 2, is a perspective view of the orthodontic bracket of the present invention, without including the means to cover the channel nor the sliding lid of the gripping means.
Figure 3:
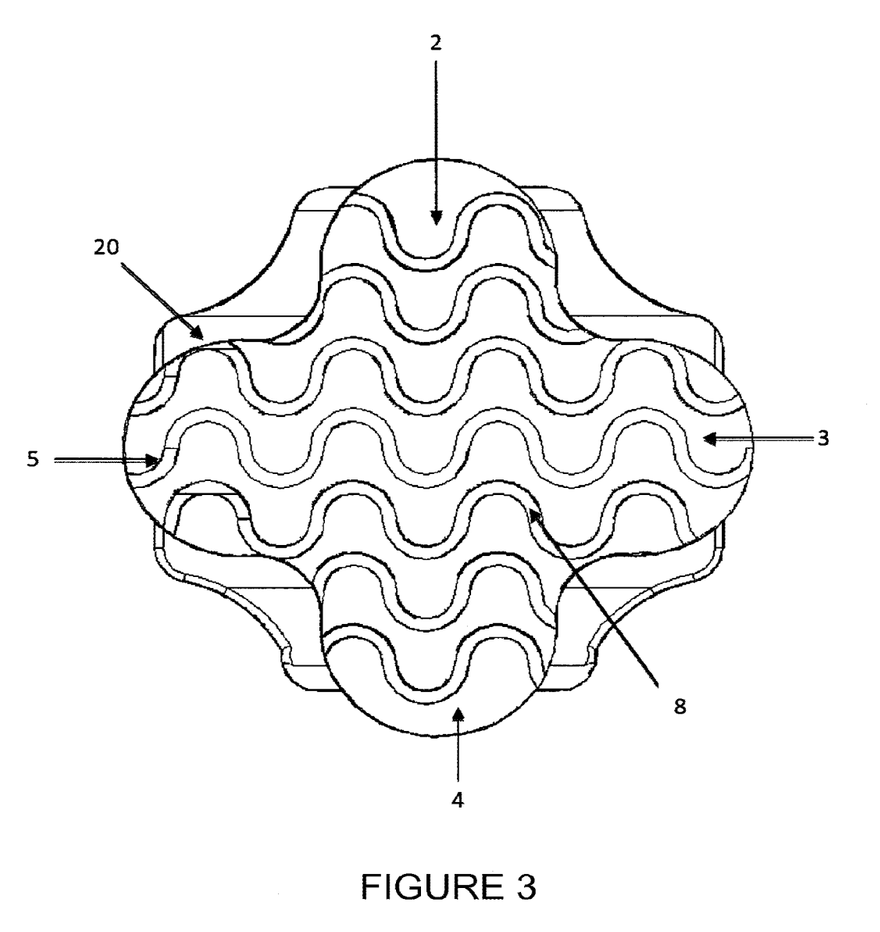
FIG. 3, is a lower view of the orthodontic bracket of the present invention.
Figure 4:
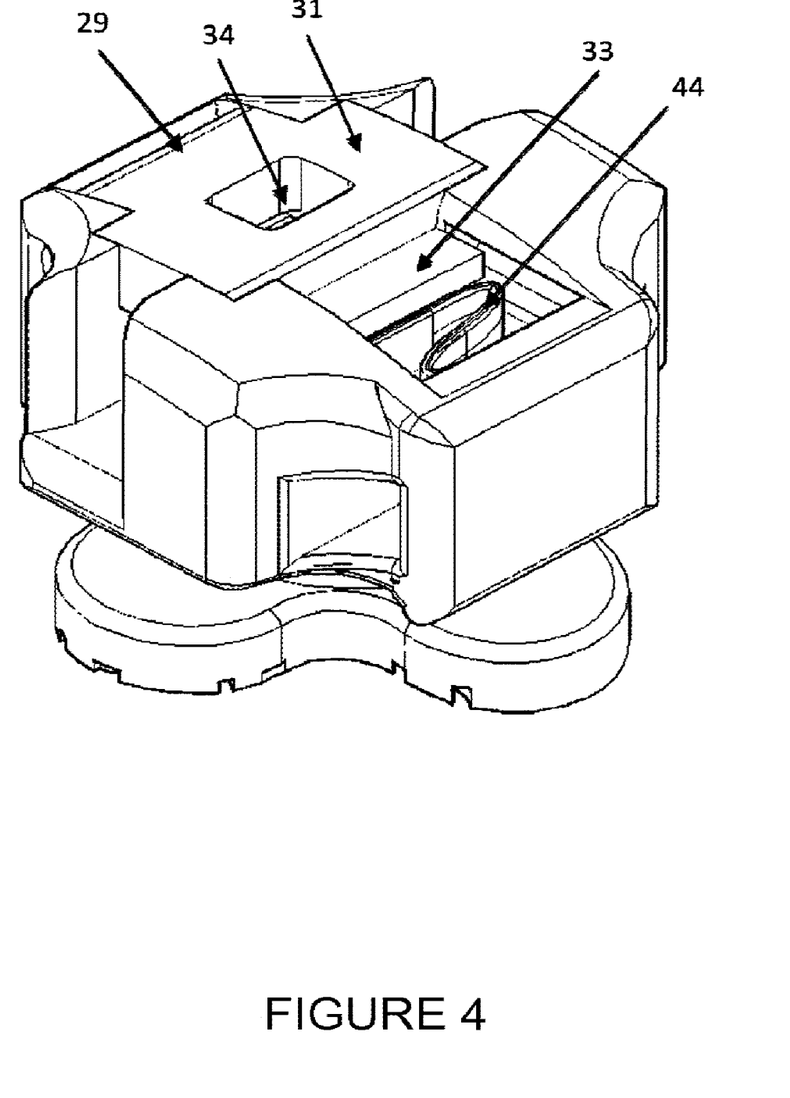
FIG. 4, is a perspective view of the orthodontic bracket of the present invention, including the means to cover the channel but without including the sliding lid of the gripping means.
Figure 5:
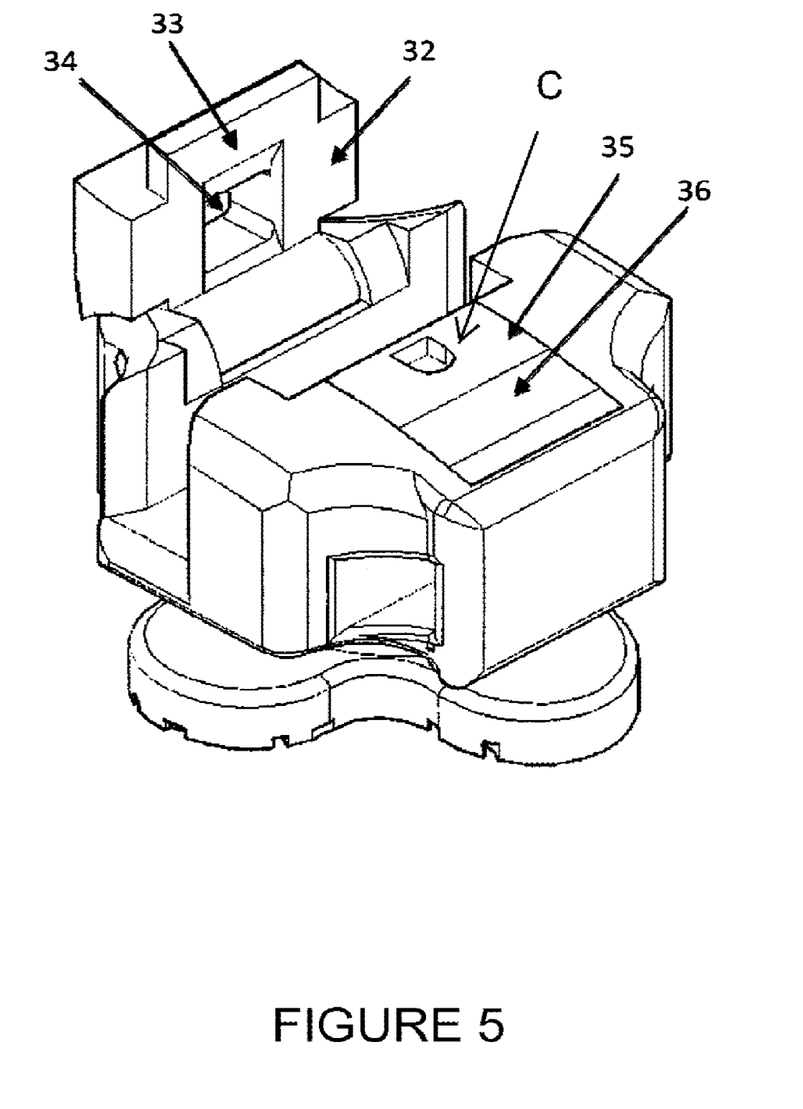
FIG. 5, is a perspective view of the orthodontic bracket of the present invention, including the means to cover the channel in an open position and including the sliding lid of the gripping means.
Figure 6:
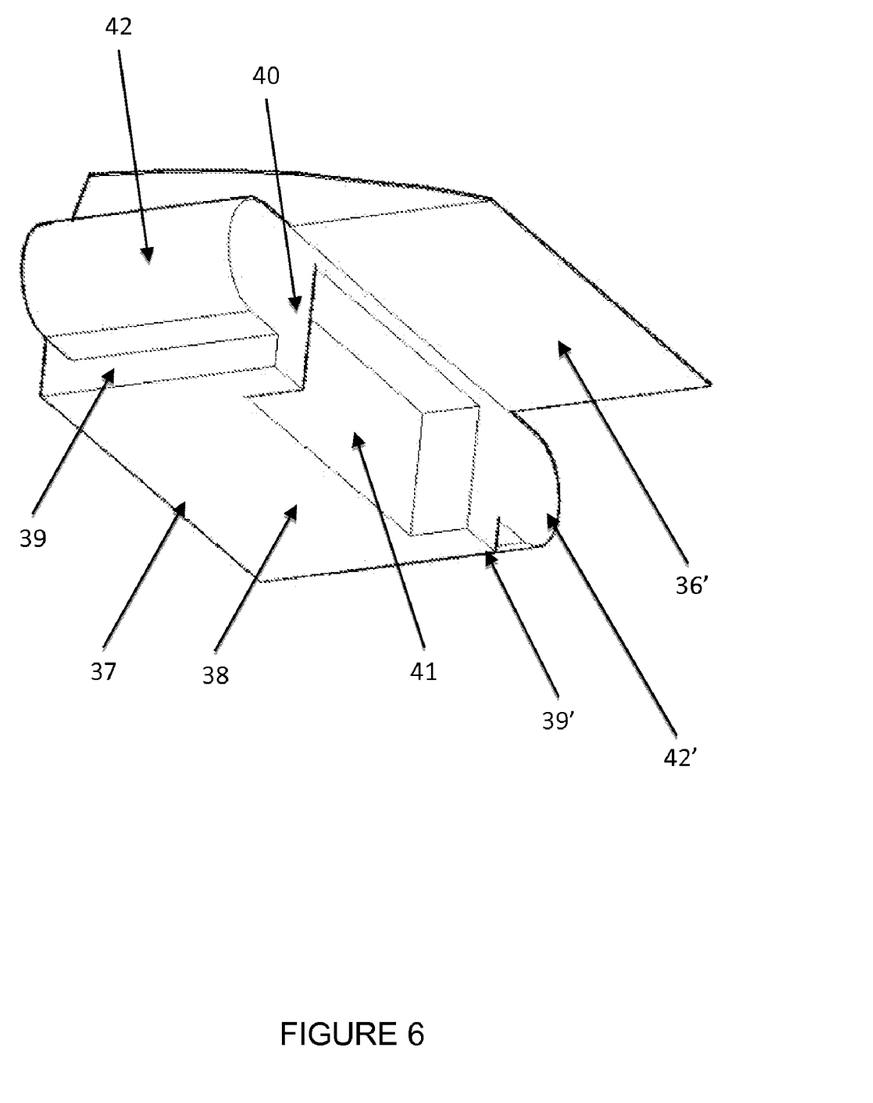
FIG. 6, is a front view in lower perspective of the sliding lid of the gripping means.
Figure 7:
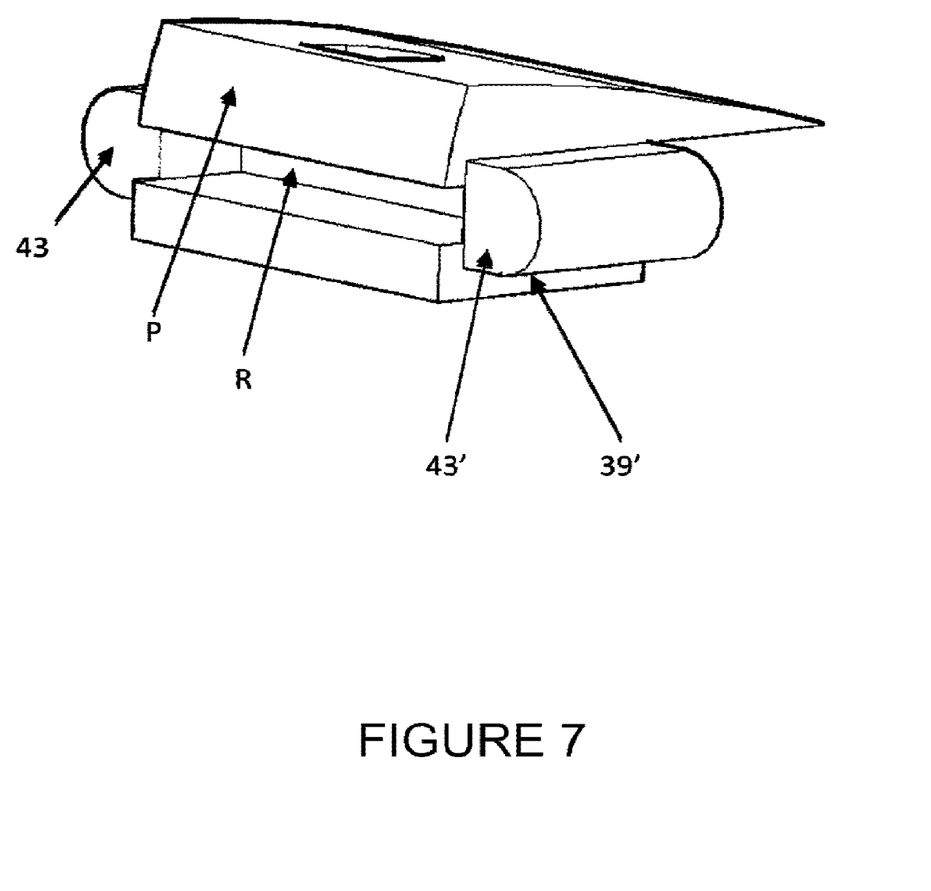
FIG. 7, is a rear perspective view of the sliding lid of the gripping means.

The orthodontic bracket of the present invention, will be described in accordance with a preferred embodiment thereof, making reference to the accompanying drawings wherein the same signs and numbers refer to the same parts of the shown drawings.

The bracket of the present invention comprises a support base 1. The support base 1 comprises a cross-shaped lower base member, comprising a first arm 2, a second arm 3, a third arm 4 and a four arm 5, each having rounded ends and edges evenly distributed; each having an upper surface 6 and a lower surface 7 having a plurality of undulated slots 8 to receive an adhesive in order to be adhered to a tooth surface.

The bracket further comprises a tubular member 9 integrally and centrally mounted on the upper surface of the lower base member, having an upper surface to receive a bracket; a quadrangular-shaped bracket member 10, having a first 11, a second 12, a third 13 and a four cut corner 14, a first 15 and a second lateral side 16, a first 17 and a second longitudinal side 18 and an upper face 19. A lower base is jointed to the upper surface of the tubular member.

A main channel 21 is opened to the upper face 19 of the bracket and crossing it longitudinally, immediately after of the first 11 and second cut corner 12, to receive a first orthodontic wire (not shown), wherein said main channel 21 has an opened quadrangular-shaped cross section.

A passage 22 longitudinally crosses the bracket, beginning from the third cut corner 13, and leading at the four cut corner 14, through which a second orthodontic wire (not shown) passes, wherein said passage has a quadrangular cross section.

A first housing 23, longitudinally placed between the first 11 and second cut corner 12 of the bracket and between the lateral side 17 and the main channel 21 in which it leads, has a first 24 and a second lateral wall 25 and a longitudinal wall 26.

A second quadrangular-shaped housing 27, longitudinally placed between the third 13 and four cut corner 14 of the bracket and between the second longitudinal side 18 and the main channel 21, wherein it leads, and over the passage 22, has a first and a second lateral wall, a rear surface and a lower surface, wherein each lateral wall includes a guide channel 28 in an upper portion along of all its length.

A covering means to cover the main channel 21, comprises a main lid 29 to cover the main channel 21, pivoting on two hinge elements 30 which form an integral part of the lateral walls 24 and 25 of the first housing and in which it is retained, said lid having an upper surface 31 and a lower surface 32, a tong 33 at a front portion, opposed where the lid is joined with the hinges 30, located at the same plane as the lower surface 32 and a quadrangular aperture 34 located in a central portion thereof, said lid 29 completely crossing the main channel 21 but covering it only partially, and wherein the whole of the tongue 33 rest in an end of the lower surface of the second housing 27 when it is at a closed portion.

A gripping means for the lid comprises a wedge-shaped sliding lid 35, slide retained on the second housing 27, and which covers it as a whole, including an upper surface 36, a lower surface 36', a quadrangular housing "C" in its upper surface 36 and a rectangular element 37 directly depending from the lower surface, located at a front portion of the lid 35, having a lower surface 38, two lateral walls 39, 39', a rear surface "P" including a housing "R" and a front surface 40

A front surface 40 includes a rectangular groove 41 and each lateral surface 39, 39' including a lateral gripping element 42, 42' each depending directly from a respective lateral surface 39, 39', and each of which is slide retained in a guide channel 28 of the second housing 27.

Each lateral gripping element 42, 42' presents a rear surface 43, 43' which are in the same plane as the rear surface "P" of the rectangular element, which, together with the lower surface 36 of the sliding lid 35, form a longitudinal lying "L"-shaped lower stop edge. Wherein said lid can slide behind of the second housing 27, until the guide channels 28 allows it and wherein said lid 35 may return sliding forward until the guide channels 28 allows it, to an original closed position wherein the second housing 27 is completely covered. The wedge shape of the slide lid 35 allows that it be adapted to the curved shape of the upper face 19 of the bracket, so that it can maintain an upper face completely smooth when the sliding lid 35 is closed.

A pushing means comprises a spring element 44 placed in the second housing 27, to push said longitudinal lying "L"-shaped lower stop edge of the sliding lid 35, so as to constantly push forward all the sliding lid 35 to the front face 17 of the bracket, this is, forwardly, maintaining it in a closed position, wherein said sliding lid 35 can be slide backwards compressing the spring element 44 between the longitudinal lying "L"-shaped lower stop edge of the sliding lid 35 and the upper surface of the lower stop wall.

The main lid 29 remains gripped in a closed position because its tong 33 is placed and gripped in the rectangular housing 41 of the sliding lid and wherein, to open the main lid 29, the sliding lid 35 must be slide behind to discover the tong 33 of the main lid 29 and could be lifted upwardly to place an orthodontic wire in the main channel 21.

The quadrangular aperture 34 of the main lid 29 located in its central portion, facilitates the insertion of a tool to open and close said lid 29 and the housing "C" of the sliding lid 35 facilitates the insertion of a tool to slide said lid 35 forward and backward to release or grip the main lid 29 in a closed position.

The main lid 29 opens to allow a fast and easy insertion of an orthodontic wire and, when closed and gripped with the sliding lid 35, avoids completely that the orthodontic wire could go out from the bracket.

Additionally, the main channel 21 can include means to reduce the friction between the wire and the channel, such as a depression in the lower wall of the channel to reduce the contact area between the wire and the channel 21.

Although it was described that the bracket of the present invention includes a passage 22 for a second orthodontic wire, in other embodiments of the invention this cannot be included or else, to include one or more passages.

Also, in other embodiments of the invention, the gripping means for the main lid 29 could comprise any other type of suitable gripping means, as for example, elements in the lid which fits under pressure in the corresponding gripping means.

Finally, it should be understood that the orthodontic bracket of the present invention is not limited to the above described embodiment and that those skilled in the art will be able, with the teachings herein established, to make changes in the orthodontic bracket of the present invention, which scope will be established exclusively by the following claims.

What is claimed is:

1. An orthodontic bracket comprising:
   a support base; and
   a bracket member mounted on said base, the bracket member comprising:
   i) a main channel opened to receive an orthodontic wire;
   ii) a covering element crossing the main channel to limit access thereto, which covering element can be i) opened, and ii) closed to cover the opened main channel; and
   iii) a gripping element for the covering element, wherein,
   the bracket member has a quadrangular shape and comprises i) a first, second, third and fourth cut corners, ii) first and second lateral sides, iii) a first and second longitudinal sides, and iv) an upper face,
   the main channel is opened to the upper face of the bracket, longitudinally crossing the bracket, immediately following the first and the second cut corners, to receive the orthodontic wire,
   the bracket member further has i) a first housing longitudinally placed between the first and second cut corners and between the first longitudinal side and the main channel, the first housing having first and second lateral walls and a longitudinal wall, and ii) a second housing having a quadrangular cross section, longitudinally placed between the third and fourth cut corners and between the second longitudinal side and the main channel,
   said second housing has first and second lateral walls, a rear surface and a lower surface, wherein each lateral wall of the second housing includes a guide channel in an upper portion throughout a length thereof,
   the covering element comprising a main lid to cover the main channel, the main lid pivoting on two hinge elements integrally formed on the two lateral walls of the first housing,
   said main lid having a lower surface, a tong in a front portion of the main lid and located in a same plane as the lower surface, a whole of the tong rests on an end of the lower surface of the second housing when the main lid is in a closed position,
   the gripping element comprising a sliding lid having a wedge shape, the sliding lid retained on the second housing and covering the second housing, the sliding lid having i) an upper surface with a quadrangular housing, and ii) a lower surface with a directly depending rectangular element, the rectangular element located at a front portion of the sliding lid, the rectangular element having a front face, a lower surface, two lateral walls, a rear surface including a housing, the front surface of the rectangular element having a rectangular groove, each lateral wall of the rectangular element including a lateral gripping element, each gripping element directly depending from a respective lateral wall, and each lateral gripping element is a slide element retained in the respective guide channel of the second housing, each lateral gripping element presenting a rear surface in a plane of the rear surface of the rectangular element, and, together with the lower surface of the sliding lid, forms a longitudinal lying L-shaped lower stop edge, the bracket member further comprises a pushing element comprising a spring element placed in the second housing, the spring element constantly pushing said longitudinal lying L-shaped lower stop edge of the sliding lid to thereby constantly push the sliding lid towards the first longitudinal side of the bracket to forwardly maintain the sliding lid in a closed position, said sliding lid is slidable backwards by compressing the spring element between the longitudinal lying L-shaped lower stop edge of the sliding lid and the rear surface of the lower stop wall, the main lid remains gripped in a closed position when the tong is located in and gripped in the rectangular housing of the sliding lid, and to open the main lid, the sliding lid is slid backwards to remove the tong from the rectangular housing and lifted upwardly to place the orthodontic wire in the main channel.

2. An orthodontic bracket according to claim 1, further comprising a passage longitudinally crossing the bracket member, the passage starting from the third cut corner and leading to the fourth cut corner, and through which passage may pass another orthodontic wire.

3. An orthodontic bracket, comprising:
a main channel to receive an orthodontic wire;
a lid crossing the main channel to limit access thereto, which lid can be i) opened to allow access to the main channel for placing the orthodontic wire, and ii) closed to cover the opened main channel having received the orthodontic wire; and
a gripping element for the lid, wherein,
the bracket member comprises i) a first, second, third and fourth cut corners, ii) first and second lateral sides, iii) a first and second longitudinal sides, and iv) an upper face,
in an open position of the lid, the main channel is opened to the upper face of the bracket, longitudinally crossing the bracket to receive the orthodontic wire,
the bracket member further has
i) a first housing longitudinally placed between the first and second cut corners and between the first longitudinal side and the main channel, the first housing having first and second lateral walls, a longitudinal wall, and two hinge elements integrally formed on the two lateral walls of the first housing, and
ii) a second housing having a quadrangular cross section, longitudinally placed between the third and four cut corners and between the second longitudinal side and the main channel, the second housing has first and second lateral walls, a rear surface and a lower surface, wherein each lateral wall of the second housing includes a guide channel in an upper portion throughout a length thereof, the lid pivots on the two hinge elements integrally formed on the two lateral walls of the first housing, said lid having a lower surface, a tong, a whole of the tong resting on an end of the lower surface of the second housing when the lid is in a closed position, the gripping element comprising a sliding lid, the sliding lid retained in the second housing, the sliding lid having i) an upper surface, and ii) a lower surface with a depending rectangular element, the rectangular element located at a front portion of the sliding lid, the rectangular element having a front face, a lower surface, two lateral walls, a rear surface including a housing, the front surface of the rectangular element having a groove, each lateral wall of the rectangular element including a lateral gripping element, each gripping element directly depending from a respective lateral wall, each lateral gripping element being a slide element retained in the respective guide channel of the second housing, each lateral gripping element presenting a rear surface that together with the lower surface of the sliding lid forms a longitudinal lying lower stop edge, the bracket member further comprises a pushing element comprising a spring element located in the second housing, the spring element pushing said longitudinal lying lower stop edge of the sliding lid to thereby push the sliding lid to the first longitudinal side of the bracket to forwardly maintain the sliding lid in a closed position, said sliding lid is slidable backwards by compressing the spring element between the longitudinal lying lower stop edge of the sliding lid and the rear surface of the lower stop wall, the lid remains gripped in a closed position due to the tong being gripped in the rectangular housing of the sliding lid, and to open the lid, the sliding lid is slid backwards to remove the tone from the rectangular housing and lifted upwardly to place an orthodontic wire in the main channel.

4. An orthodontic bracket according to claim 3, further comprising a passage longitudinally crossing the bracket member, the passage starting from the third cut corner and leading to the fourth cut corner, through which passage may pass another orthodontic wire.

* * * * *